(12) United States Patent
Enge et al.

(10) Patent No.: US 10,507,289 B2
(45) Date of Patent: Dec. 17, 2019

(54) MEDICAMENT DELIVERY DEVICE

(71) Applicant: CAREBAY EUROPE LTD, Sliema (MT)

(72) Inventors: Kasper Enge, Järfälla (SE); Gunnar Elmén, Huddinge (SE); Anders Holmqvist, Värmdö (SE)

(73) Assignee: SHL MEDICAL AG, Zug (CH)

( * ) Notice: Subject to any disclaimer, the term of this patent is extended or adjusted under 35 U.S.C. 154(b) by 188 days.

(21) Appl. No.: 15/553,647

(22) PCT Filed: Feb. 2, 2016

(86) PCT No.: PCT/EP2016/052146
§ 371 (c)(1),
(2) Date: Aug. 25, 2017

(87) PCT Pub. No.: WO2016/139023
PCT Pub. Date: Sep. 9, 2016

(65) Prior Publication Data
US 2018/0050159 A1    Feb. 22, 2018

(30) Foreign Application Priority Data

Mar. 5, 2015 (EP) .................................. 15157824

(51) Int. Cl.
*A61M 5/315* (2006.01)
*A61M 5/24* (2006.01)
*A61M 5/31* (2006.01)

(52) U.S. Cl.
CPC ...... *A61M 5/31536* (2013.01); *A61M 5/2459* (2013.01); *A61M 5/3155* (2013.01);
(Continued)

(58) Field of Classification Search
CPC .......... A61M 5/31536; A61M 5/31541; A61M 5/31548; A61M 5/3155; A61M 5/31551;
(Continued)

(56) References Cited

U.S. PATENT DOCUMENTS

| 5,226,896 A * | 7/1993 | Harris ............... A61M 5/31551 604/208 |
| 2004/0127858 A1* | 7/2004 | Bendek ............. A61M 5/31541 604/208 |

(Continued)

FOREIGN PATENT DOCUMENTS

| WO | 2006/130098 A1 | 12/2006 |
| WO | 2008/067467 A2 | 6/2008 |

OTHER PUBLICATIONS

International Search Report and Written Opinion for Int. App. No. PCT/EP2016/052146, dated Apr. 20, 2016.

*Primary Examiner* — Nathan R Price
*Assistant Examiner* — Anh Bui
(74) *Attorney, Agent, or Firm* — McDonnell Boehnen Hulbert & Berghoff LLP

(57) ABSTRACT

A medicament delivery device is presented having a housing, a medicament container holder, arranged movable in relation to the housing and capable of accommodating a medicament container. An activator is arranged in the housing and capable of, upon activation, acting on a medicament container for expelling a dose of medicament, where the activator has a plunger rod, a manually operable dose setting nut rotatably connected to the housing and arranged with first threads. Second threads are arranged on the medicament container holder being arranged to cooperate with said dose setting nut, wherein operation of the dose setting nut will cause the medicament container holder with the medicament (Continued)

container to move towards the plunger rod for setting a dose of medicament to be delivered.

20 Claims, 7 Drawing Sheets

(52) U.S. Cl.
CPC .... *A61M 5/31541* (2013.01); *A61M 5/31548* (2013.01); *A61M 5/31551* (2013.01); *A61M 5/31553* (2013.01); *A61M 5/31555* (2013.01); *A61M 5/31585* (2013.01); *A61M 2005/3126* (2013.01); *A61M 2005/3154* (2013.01)

(58) Field of Classification Search
CPC .......... A61M 5/31553; A61M 5/31555; A61M 2005/3154
See application file for complete search history.

(56) References Cited

U.S. PATENT DOCUMENTS

| | | | | |
|---|---|---|---|---|
| 2009/0299297 A1* | 12/2009 | Moller | ............... | A61M 5/24 604/211 |
| 2012/0209208 A1* | 8/2012 | Stefanski | ............ | A61M 5/20 604/189 |

* cited by examiner

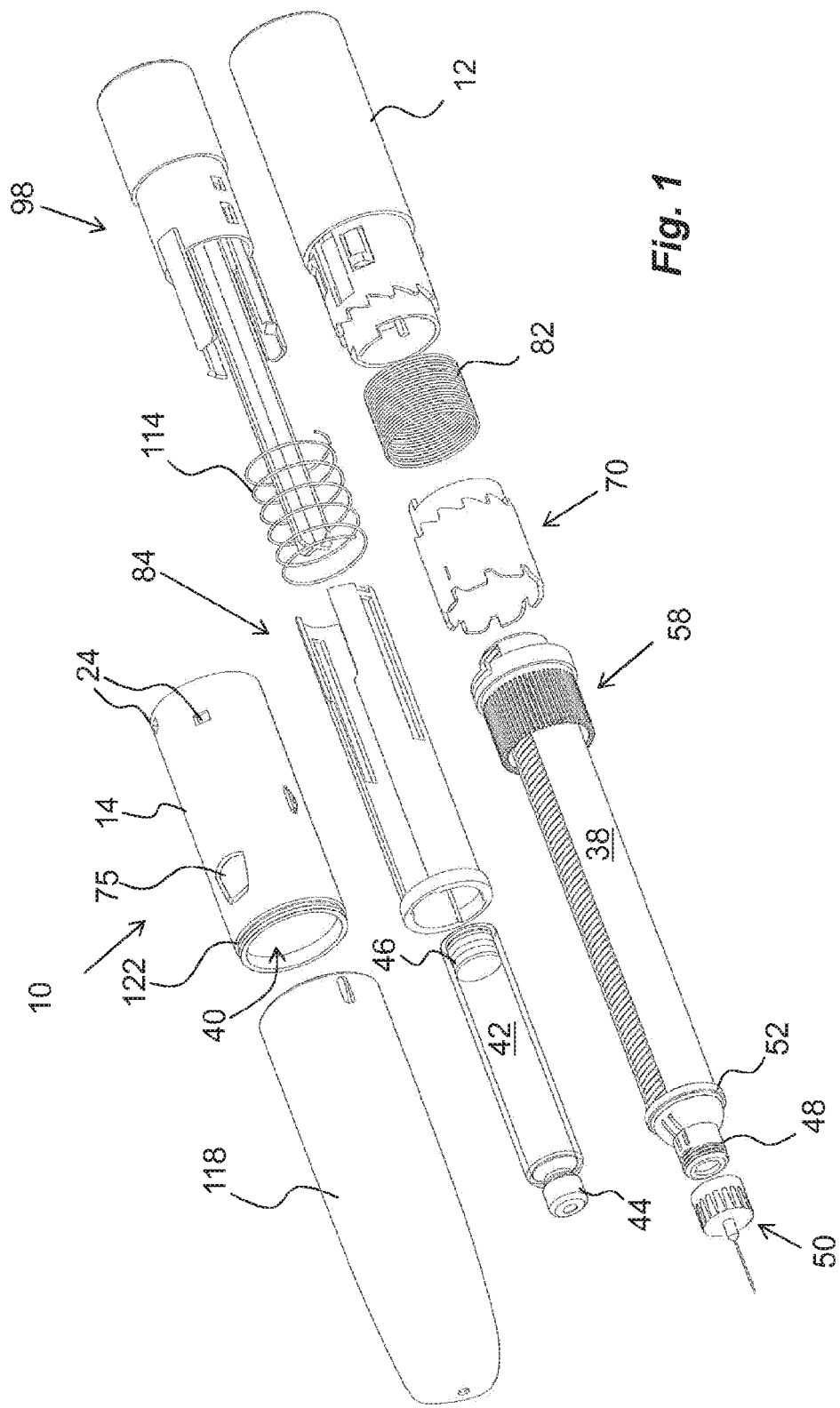

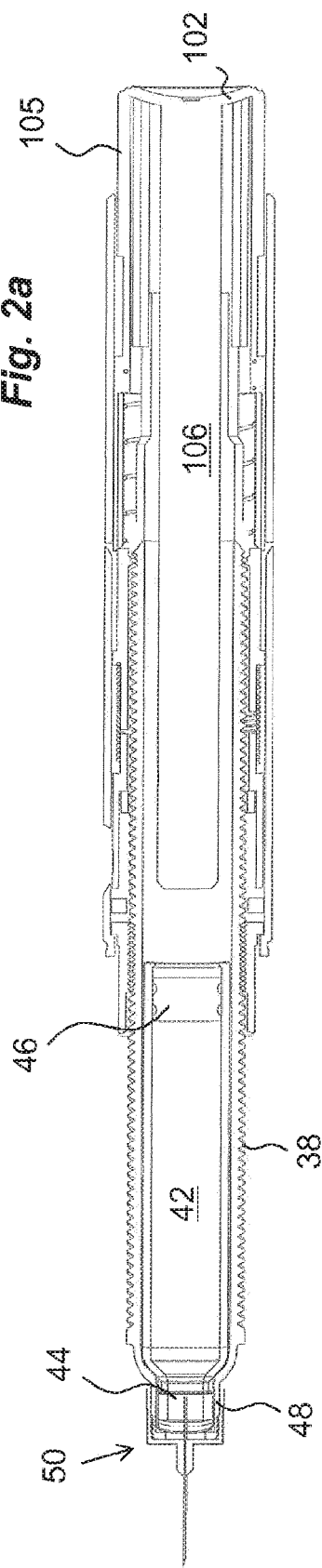

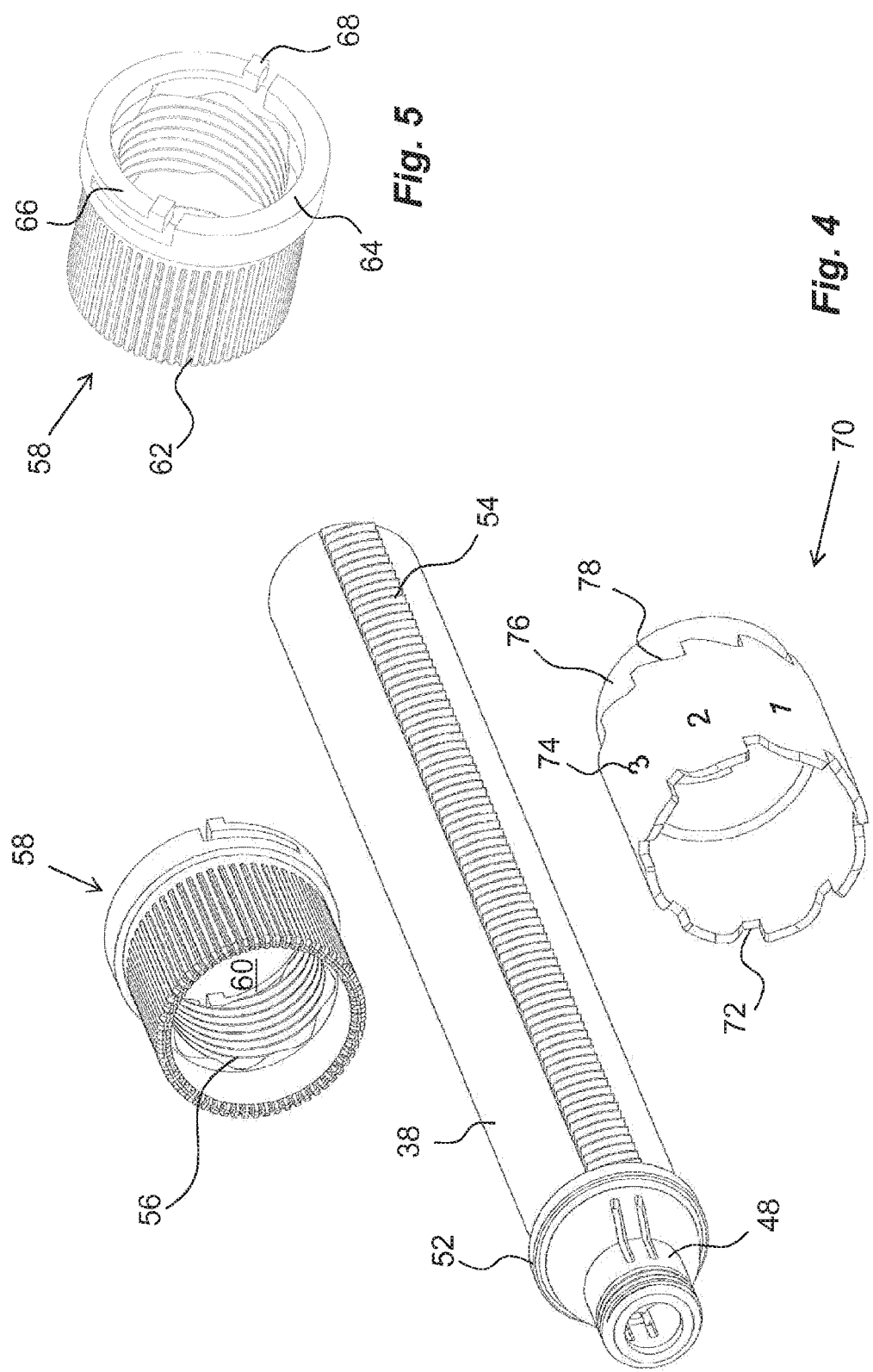

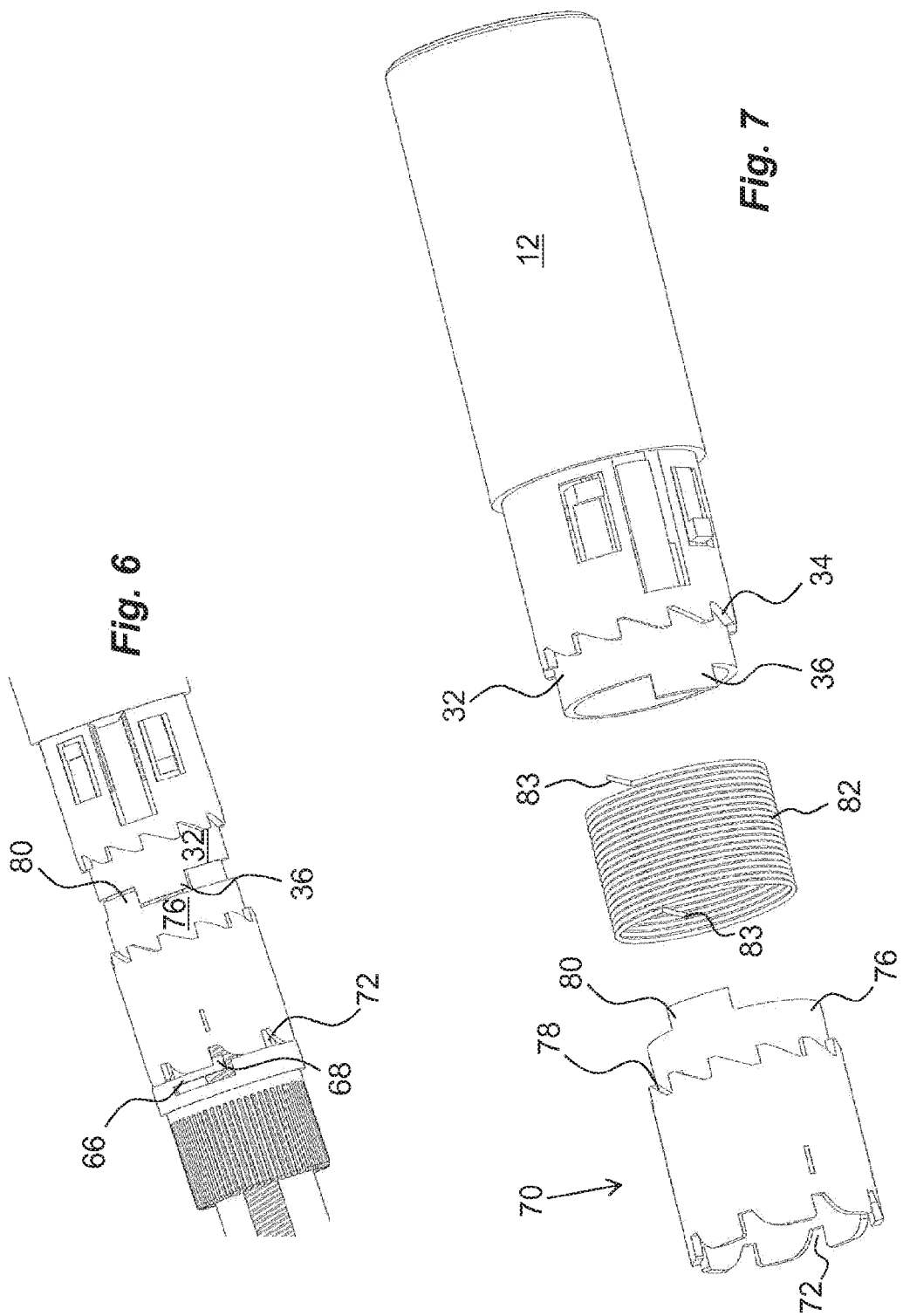

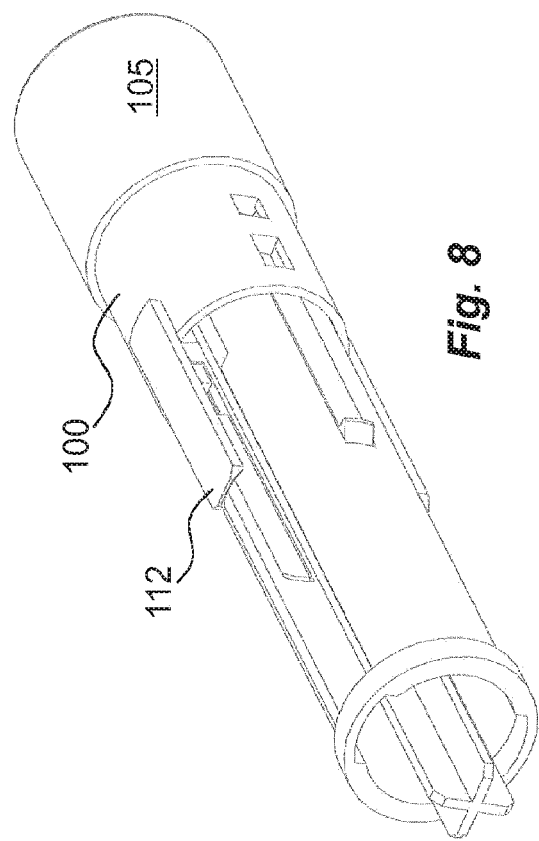
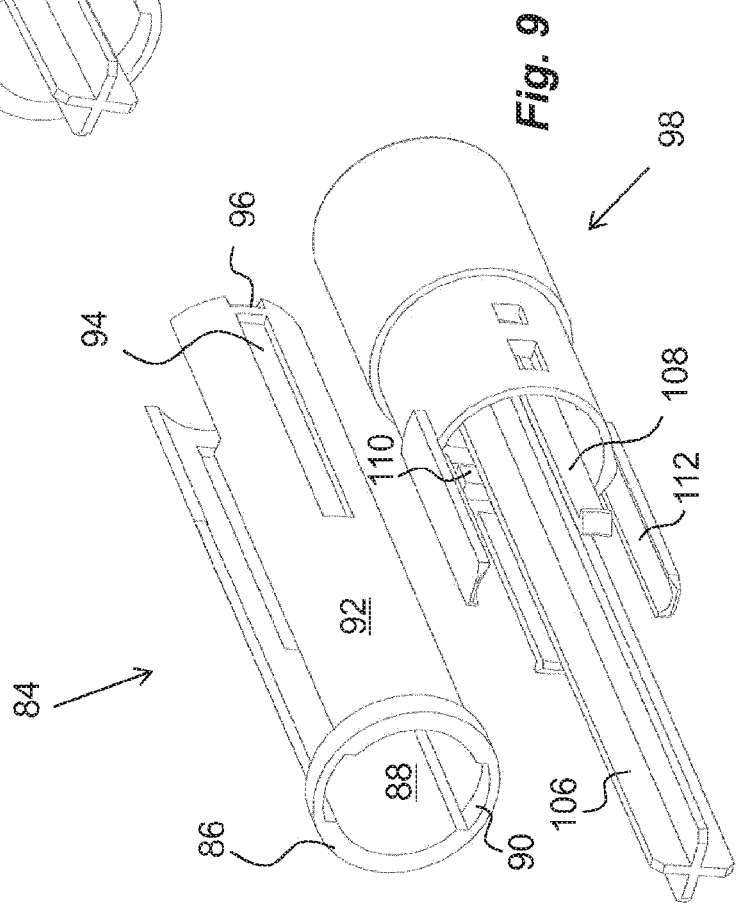

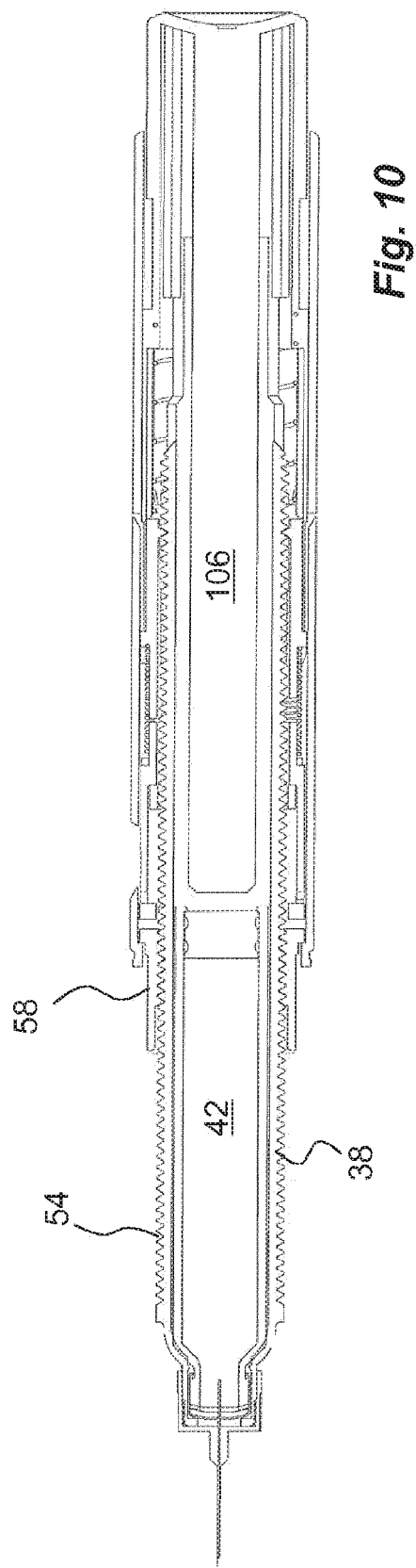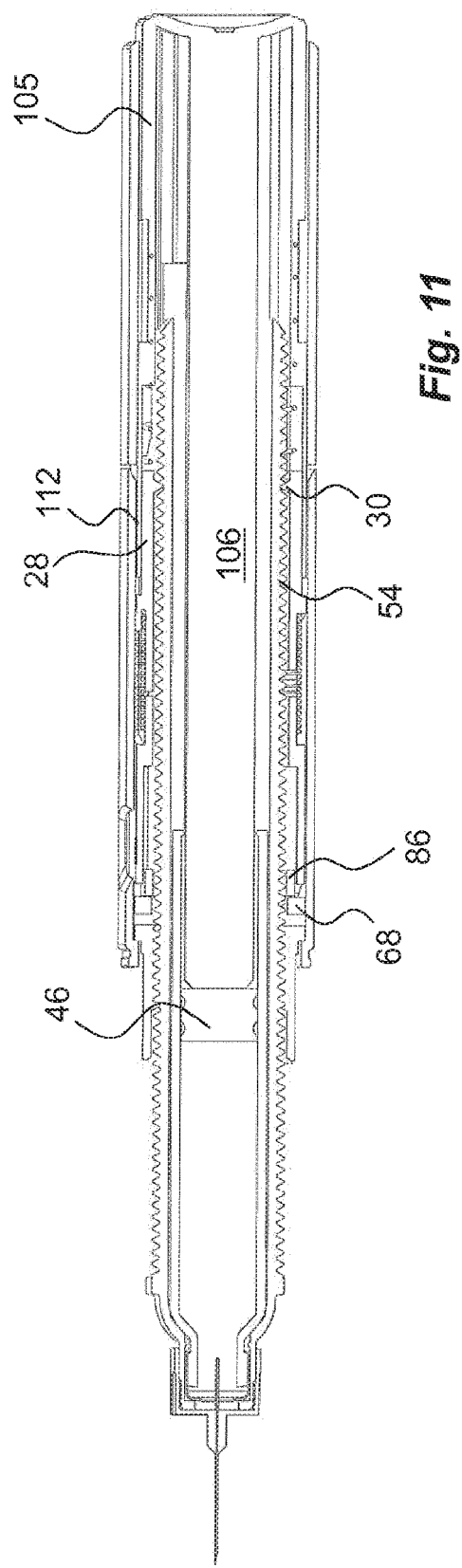

MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2016/052146 filed Feb. 2, 2016, which claims priority to European Patent Application No. 15157824.2 filed Mar. 5, 2015. The entire disclosure contents of these applications are herewith incorporated by reference into the present application.

TECHNICAL FIELD

The present disclosure relates to a medicament delivery device and in particular a medicament delivery device that is capable of having its length reduced during use of the device.

BACKGROUND

Many medicament delivery devices that are out on the market for self-administering of doses of medicament are arranged with dose setting features. These may be parts of the medicament delivery device that is operable in relation to other parts, such as dose drums that are rotated in relation to a housing. In some solutions the different housing parts are moved in the longitudinal direction in relation to each other when a dose is set. For instance, the document U.S. Pat. No. 5,226,896 discloses an injection pen comprising a collar and a syringe housing in threaded engagement with each other. In order to set a dose of medicament, the syringe housing is rotated in relation to the collar, whereby the syringe housing is moved inside the collar, making the housing of the device shorter. On the other hand, when setting a dose, a distal end of the device comprising a cap attached to a distal end of a plunger rod is extended in the distal direction. This is because the proximal end of the plunger rod is in contact with a stopper in a syringe filled with medicament, and when the syringe housing is moved in the distal direction, so does the stopper, plunger rod and cap due to the incompressibility of the medicament in the syringe. Thus, the device retains more or less the same length during the setting of a dose. When then an injection is to be performed, the cap with its plunger rod is pressed linearly in the proximal direction, causing a dose delivery. Further, the pressure on the medicament in the syringe during dose setting may cause a leakage of medicament when an injection needle is attached to the proximal end of the syringe.

Document WO 2006/130098 displays a medicament delivery device comprising a proximal cartridge housing comprising a cartridge. The proximal housing part is threadedly connected to a distal back cover provided with a dose indication drum. For setting a dose of medicament, the back cover is rotated in relation to the proximal cartridge housing. When the back cover is rotated, a plunger rod spring is compressed. Further, a servo spring in the form of a clock spring is also arranged to aid the plunger rod in the injection operation, and is tensioned when the back cover is rotated. In order to deliver a dose, the proximal end is pressed against and injection site, whereby the plunger rod spring and the servo spring are released by a needle shield affecting a release mechanism, which springs force the plunger rod in the proximal direction, whereby a dose of medicament is delivered.

The device according to WO 2006/130098 is rather bulky and difficult to handle and is provided with double springs which makes a somewhat complicated device in particular if the device is to be used as a disposable medicament delivery device.

Regarding device size and functional features, especially regarding disposable medicament delivery devices, there are further developments to be made.

SUMMARY

In the present application, when the term "distal part/end" is used, this refers to the part/end of the device, or the parts/ends of the members thereof, which during use of the device is located the furthest away from the medicament delivery site of the patient. Correspondingly, when the term "proximal part/end" is used, this refers to the part/end of the device, or the parts/ends of the members thereof, which during use of the device is located closest to the medicament delivery site of the patient.

The aim of the present disclosure is to remedy the drawbacks of the state of the art devices. This aim is obtained by a medicament delivery device according to the features of the independent patent claim. Preferable embodiments of the disclosure form the subject of the dependent patent claims.

According to one aspect of the disclosure, it comprises a medicament delivery device comprising a housing and a medicament container holder, arranged movable in relation to said housing and capable of accommodating a medicament container. The medicament container could comprise a number of different types that may be used for administering doses of medicament, such as syringes, medicament cartridges, medicament delivery members such as injection needles, mouth pieces or nasal pieces, nebulizers etc.

An activator may preferably be arranged in the housing that is capable of acting on a medicament container for expelling a dose of medicament when the activator is operated. The activator may preferably then comprise a plunger rod that can act on the medicament container.

According to a preferable solution, a manually operable dose setting nut may be rotatably connected to the housing and being arranged with threads. These threads may preferably be arranged to cooperate with threads arranged on the medicament container holder such that operation of the dose setting nut will cause the medicament container holder with the medicament container to move towards the plunger rod for setting a dose of medicament to be delivered. Thus as the medicament container is moved, the medicament delivery device becomes shorter during dose setting. In order to guide the medicament container holder there is preferably a rotational lock arranged between the medicament container holder and the housing.

In order for the user to obtain information during the dose setting operation, the medicament delivery device may comprise a dose setting drum arranged with indicia, which indicia indicates the size of the dose that is set. Further, the medicament delivery device may further comprise a connection mechanism arranged between the dose setting nut and the dose drum in a manner where the dose drum is rotated together with the dose setting nut when operated for setting a dose.

According to a favourable solution, the connection mechanism may be arranged as a releasable connection. Preferably the connection mechanism may comprise resiliently arranged protrusions on one of the dose nut or dose drum engageable with cut-outs on the other of the dose drum or dose nut.

In order to reset the dose drum after a dose of medicament has been delivered, the medicament delivery device may further comprise a return force element operably connected to the dose drum such that the return force element is tensioned when a dose is set. The return force element will then rotate back the dose drum when the dose drum is released from the dose nut at the end of a dose delivery operation. In that respect, the activator may be operably connected to a release mechanism, wherein, when the activator is activated, the release mechanism is arranged to act on the connection mechanism for releasing the dose drum from the dose setting nut, whereby the return force element is capable of moving the dose drum back to its initial position.

Preferably the medicament delivery device may further comprise a dose limiting mechanism operably arranged to the dose nut and capable of limiting the maximum dose to be set. This ensures that the user cannot set a dose size that may be dangerous or adversely affect the user.

According to one feasible solution, the dose limiting mechanism may comprise a stop ledge arranged to interact with a stop ledge on the housing, wherein the turning of the dose nut will bring the stop ledges in contact with each other within one turn of the dose setting nut, limiting the maximum dose to be set.

The medicament delivery device may further comprise a dose positioning mechanism operably arranged between the medicament container holder and the housing, capable of providing distinct fixed positions in the longitudinal direction of the medicament container holder in relation to the housing when a dose is set. According to a feasible solution, the dose positioning mechanism may comprise positioning elements arranged on the housing, capable of engaging the threads of the medicament container holder. In this manner, the medicament holder cannot move in relation to the housing for example when a dose of medicament is being delivered.

In order to further enhance the locking of the position between the medicament container holder and the housing, the activator may comprise a locking mechanism operably connected to the dose positioning mechanism such that, when the activator is operated, the positioning elements are in locked engagement with the threads of the medicament container holder. In this manner, the positioning elements cannot be forced out of engagement with the threads, ensuring a very firm locking of the medicament container holder with the housing.

In order not to be able to set a dose that is higher than the remaining dose of the medicament container, the medicament delivery device may further comprise a last dose mechanism operably arranged to the dose nut and capable of limiting the maximum dose to be set to the remaining quantity of medicament in the medicament container.

According to one possible solution, the last dose mechanism may comprise a stop ledge in a proximal area of the medicament container holder, arranged to come in contact with, and limit the movement, of the dose setting nut.

The medicament delivery device may further be arranged such that the activator comprises a manually operable push button extending in a distal direction through the housing. The user may then readily perform a dose delivery operation by merely pressing the push button in the proximal direction. In that respect, the activator may preferably comprise a return force element arranged to return the activator after delivery of a dose of medicament.

These and other aspects of, and advantages with, the present disclosure will become apparent from the following detailed description of the disclosure and from the accompanying drawings.

BRIEF DESCRIPTION OF DRAWINGS

In the following detailed description of the disclosure, reference will be made to the accompanying drawings, of which FIG. 1 is an exploded view of one embodiment of the present disclosure, FIG. 2 is a longitudinal cross-section of the medicament delivery device of FIG. 1, FIGS. 3-9 are detailed views of components comprised in the embodiment of FIG. 1, and FIGS. 10-11 are longitudinal cross-sectional views of different functional positions.

DETAILED DESCRIPTION

Figure 3A:
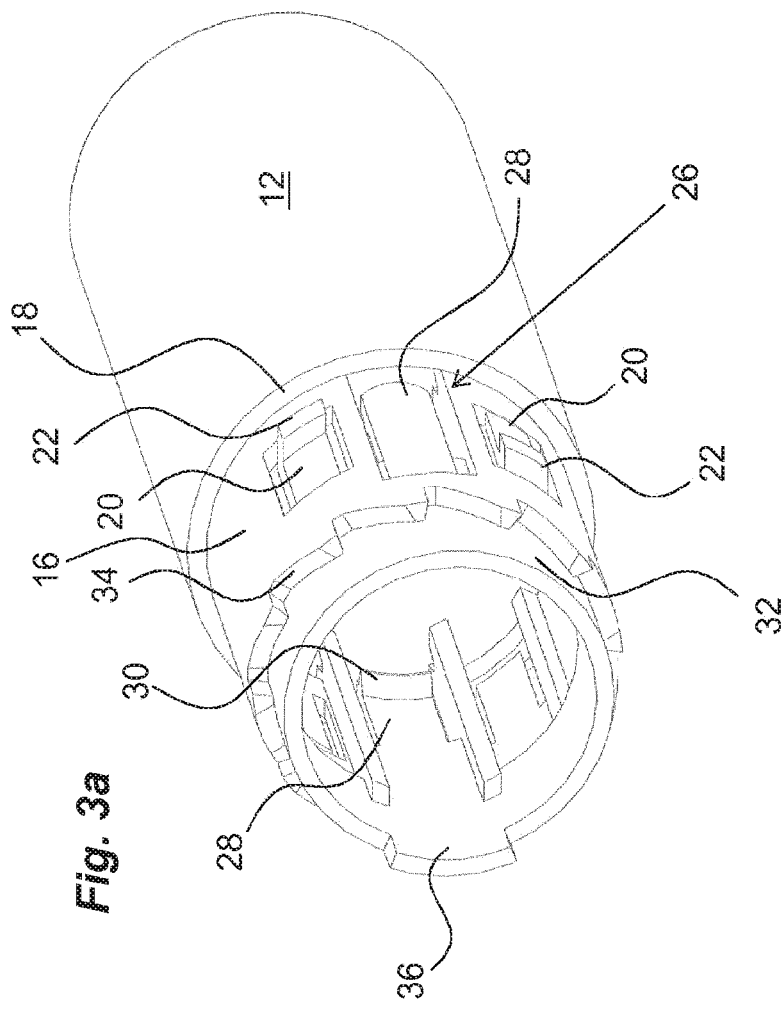

The embodiment of a medicament delivery device 10 shown in the drawings comprises a generally tubular housing that in the embodiment shown is in a distal housing part 12 and proximal housing part 14. The distal housing part 12 is arranged with a first proximal area 16, FIG. 3, having a diameter somewhat smaller than the rest of the housing part, creating a proximally directed circumferential ledge 18. The first proximal area 16 is further arranged with a number of arms 20 flexible in a generally radial direction and being provided with outwardly extending protrusions 22 at their free ends. These protrusions 22 are arranged to be snap-fitted into recesses 24, FIG. 1, in a distal area of the proximal housing part 14, such that the two housing parts are connected to each other.

Figure 3B:
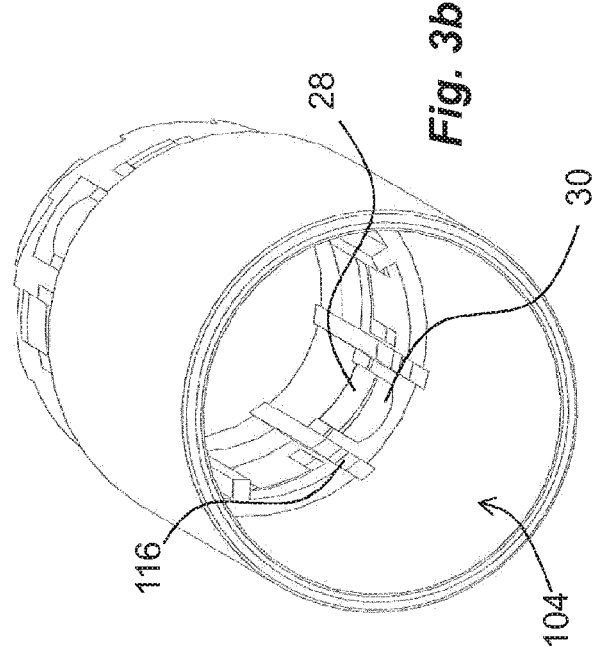

The distal housing 12 part is further arranged with a dose position mechanism 26, which comprise proximally directed tongues 28, FIG. 3. The free ends of the tongues 28 are arranged with inwardly directed pointed protrusions 30, the function of which will be described below. The first proximal area 16 is further arranged with a second proximal area 32 at its proximal end arranged with a reduced diameter, creating a proximally directed ledge 34. The proximally directed ledge 34 is in turn arranged with a saw-tooth pattern, i.e. straight longitudinally extending parts and inclined parts as seen in FIG. 3a. At the proximal end surface of the distal housing part a proximally directed first stop ledge 36 is arranged. The function of the above mentioned elements will be described below.

The medicament delivery device is further arranged with a generally tubular, elongated, medicament container holder 38, FIGS. 1 and 4, which is arranged to fit into the housing parts via a proximal passage 40 in the proximal housing part 14. The medicament container holder 38 is designed to accommodate a medicament container 42, which medicament container is arranged with a neck portion 44 arranged with a penetrable septum and stopper 46 movable inside the medicament container 42. When fitted into the medicament container holder 38, its neck portion 44 fits into a proximal neck portion 48 of the medicament container holder 38 as seen in FIG. 2. The neck portion 48 of the medicament container holder 38 is arranged with attachment elements for releasably attaching a medicament delivery member 50, in the embodiment shown an injection needle. The attachment elements may be threads as shown, but may instead be of other types, such as bayonet fittings, luer connection etc. An annular shoulder 52 is further arranged on an outer surface of the medicament container holder 38 at a proximal area thereof.

The medicament container holder 38 is arranged with two elevated bands of thread segments 54 on its outer surface, on opposite sides thereof, FIG. 4. The thread segments 54 are arranged to cooperate with threads 56 on a generally tubular dose nut 58. These threads 56 are arranged in a central passage 60 in the dose nut 58. The outer surface of the dose nut 58 is preferably arranged with grip elements such as ribs 62. The dose nut 58 is further arranged with a distally directed circumferential end surface 64, FIG. 5. On the end surface 64, two generally circumferentially extending arms 66 are arranged, which arms 66 are flexible in the longitudinal direction of the medicament delivery device. The free ends of the arms 66 are provided with distally directed protrusions 68.

Arranged distal of the dose nut 58 is a generally tubular dose drum 70, FIG. 4. The dose drum 70 has a proximally directed end surface, which end surface is arranged with cut-outs 72 around its circumference. The cut-outs 72 have a shape with one side wall which is straight and extending in the proximal direction and one side wall which is convexly curved. The side walls of the cut-outs 72 are to cooperate with the arms 66 and the protrusions 68 of the dose nut 58 as seen in FIG. 6 and as will be described. The outer surface of the dose drum 70 is arranged with indicia 74 such as numbers, which indicia 74 are shown in an opening or a window 75 in the distal housing part 12, FIG. 1.

A distal area 76 of the dose drum 70 is arranged with a reduced diameter, creating a distally directed ledge 78. The ledge 78 is in turn arranged with a saw-tooth pattern, i.e. straight longitudinally extending parts and inclined parts as seen in FIG. 5. At the distal end surface of the dose drum 70 a distally directed stop ledge 80 is arranged, FIG. 7. The distal area with reduced diameter 76 is arranged adjacent the second proximal area 32 of the distal housing part 12, wherein the areas with reduced diameter 32, 76 have generally the same diameters. The stop ledges 36, 80 are further placed next to each other as seen in a circumferential direction, FIG. 6. A torsion spring 82 is arranged along the both areas with reduced diameter 32, 76, where the free ends of the torsion spring 82 are provided with inclined portions 83 that generally correspond to the inclined parts of the saw-tooth ledges and will engage and lock the ends of the spring 82.

Further, a release mechanism 84 is arranged in the medicament delivery device, FIGS. 1 and 9. It comprises a ring-shaped proximal element 86 having a passage 88 with a diameter somewhat larger than the diameter of the proximal housing part, where the latter extends into the passage. The passage 88 is further arranged with cut-outs 90 in which the bands of thread segments 54 of the medicament container holder 38 fit, creating a rotational lock between the medicament container holder 38 and the release mechanism 84. The release mechanism 84 is further arranged with two distally extending arms 92 attached to the ring-shaped element. The arms 92 are arranged with longitudinally extending slits 94 at their distal areas. At the distal end of the slits 94, bridges 96 are created.

The release mechanism 84 is arranged to be attached to an activator 98. The activator 98 comprises a generally tubular body 100 having a distal part, with an end wall 102, FIG. 2, that extends through a distally directed passage 104 in the distal housing part 12, FIG. 3*b*. The distal part of the activator 98 will function as a manually operable activation button 105 as will be described. A plunger rod 106 is attached to, or made integral with, a proximally directed surface of the end wall 102, wherein the plunger rod 106 is extending in the proximal direction towards the medicament container 42, as can be seen in FIG. 2*a*. The activator 98 is further arranged with proximally extending guide arms 108, which guide arms 108 are arranged to fit into the slits 94 of the release mechanism 84. Further, the inner surface of the body 100 of the activator 98 is arranged with a ledge 110, positioned in the extension of the slit 94, wherein the bridge 96 fits on the distal side of the ledge 110, as seen in FIG. 2*b*. The guide arms 108 in the slits 94 and the bridge 96 distal of the ledge 110 provide a locking of the release mechanism 84 with the activator 98.

The activator 98 is further arranged with a locking mechanism in the form of proximally extending tongues 112, the function of which will be described below. A return spring 114, FIG. 2, is arranged between a proximally directed end surface of the body 100 of the activator 98 and distally directed surfaces of ledges 116 of the distal housing part 12, FIG. 3*b*. The medicament delivery device also comprises a protective cap 118, FIG. 12, that is releasibly attached to the proximal end. The protective cap is held in place by an annular ledge 120 on the inner surface of the protective cap fitting into an annular groove 122 on the outer surface of the distal housing part.

The device is intended to function as follows. When the user is to administer a dose of medicament, the protective cap 118 is removed. For setting a dose the dose nut 58 is rotated in relation to the housing. Because of the threaded connection between the dose nut 58 and the medicament container holder 38, the medicament container holder 38 will move, together with the medicament container 42, in the distal direction. The arms 66 of the dose nut 58 are in engagement with the side surfaces of the cut-outs 72 of the dose drum 70, whereby the dose drum 70 will also rotate. The indicia 74 on the dose drum will be displayed through the window 75, indicating the set dose.

As the dose drum 70 rotates the torsion spring 82 will be tensioned because one free end of the spring is in engagement with the saw-toothed ledge 78 of the dose drum 70 and the other free end is in engagement with the stationary saw-toothed ledge 34 of the distal housing part 12. The maximum dose to be set is limited by the distally directed stop ledge 80 of the dose drum and the proximally directed stop ledge 36 of the distal housing part 12 in that the distally directed stop ledge 80 will be moved in contact with the proximally directed stop ledge 36 when the dose drum 70 has been rotated a certain distance, which is less than a full turn. However, within this rotational range, it is possible to turn up and down the dose size as desired by the user.

It is further to be noted that the plunger rod 106 is designed and positioned such in an unaffected initial position that its proximal end does not come in contact with the stopper 46 of the medicament container 42 even when a maximum dose has been set, wherein the medicament container holder 38 and the medicament container 42 have been moved a maximum distance in the distal direction. During the setting of the dose, when the medicament container holder 38 is moved in the distal direction, the tongues 28 with the protrusions 30 of the dose position mechanism 26 will ride over the thread segments 54, causing an audible response. The dose size snaps protrusions 30 engagement with the thread segments 54 will also define exact and distinct dose size positions.

When the dose has been set, a medicament delivery member 50 is attached to the proximal end of the medicament container holder 38. In the embodiment shown the medicament delivery member 50 is an injection needle that is screwed onto the medicament container holder 38. The injection needle is then arranged with a distally directed pointed end that will penetrate the septum of the medicament container 42. The user then places the medicament delivery device at the dose delivery site, causing a penetration of the injection needle. The activation button 105 of the activator 98 is then pressed in the proximal direction. First, the plunger rod 106 will be moved proximally a certain distance without being in contact with the stopper 46 of the medicament container 42, where the distance is dependent on the set dose, wherein a larger dose will provide a shorter distance and a smaller dose a larger distance. During the movement of the activator 98 in the proximal direction the tongues 112 will move outside the dose position mechanism 26 as seen in a radial direction, FIG. 11, whereby the dose position mechanism 26 are prevented from being moved out of engagement with the thread segments 54. The engagement also prevents the medicament container holder 38 from being moved out of position during injection.

When the plunger rod 106 has moved this distance, it comes in contact with the stopper 46 and pushes it in the proximal direction, causing delivery of the set dose of medicament through the medicament delivery member 50. The movement of the activator 98 in the proximal direction will also cause the release mechanism 84 to be moved in the proximal direction wherein its proximal end surface 86 is moved in contact with the arms 66 of the dose nut 58 whereby these are pushed in the proximal direction and moved out of engagement with the cut-outs 72 of the dose drum 70. The dose delivery is then stopped when the proximal surface of the release mechanism 84 abuts the distal end surface of the dose nut 58. Further, the release of the dose drum 70 will cause it to rotate back to its initial position by the force of the torsion spring 82. The stop of the activator 98 and the return of the dose drum 70 will inform the user that it is safe to remove the medicament delivery device from the dose delivery site. The user then releases the activator 98, whereby it is moved distally back to its initial position by the return spring 114, which is defined by a distally directed surface of the ring-shaped element 86 of the release mechanism 84 abutting an annular proximally directed ledge on the inner surface of the distal housing part. The user then replaces the protective cap 118, either with the medicament delivery member on, or with the medicament delivery member removed and discarded.

Thus, each time the user is to administer a dose of medicament the above described steps are performed. When the medicament container is almost empty, it is not possible to set a dose larger than the remaining dose. This is due to the shoulder 52 on the medicament container holder 38, because when the medicament container holder 38 is moved in the distal direction during dose setting, the shoulder 52 will be moved in contact with a proximally directed surface of the dose nut 58, preventing any further movement of the medicament container holder 38 and thereby the medicament container 42. When the medicament container 42 is empty, the medicament delivery device 10 is discarded in a safe way.

It is to be understood that the embodiment described above and shown in the drawings is to be regarded only as a non-limiting example of the disclosure and that it may be modified in many ways within the scope of the patent claims.

The invention claimed is:

1. A medicament delivery device comprising a housing:
    a medicament container holder, arranged movable in a distal direction relative to the housing and configured to hold a medicament container;
    an activator arranged in the housing in an initial position and movable in a proximal direction when activated to act on the medicament container for expelling a dose of medicament, where after expulsion of the dose of medicament, the activator is released and moves distally back to the initial position, where said activator comprises a plunger rod;
    a manually operable dose setting nut rotatably connected to the housing and arranged with first threads,
    wherein second threads arranged on the medicament container holder cooperate with the first threads on the dose setting nut,
    wherein operation of the dose setting nut will cause the medicament container holder and the medicament container to move in the distal direction relative to and towards the plunger rod during setting of a dose of medicament to be delivered.

2. The medicament delivery device according to claim 1, further comprising a rotational lock arranged between said medicament container holder and said housing.

3. The medicament delivery device according to claim 1, further comprising a dose setting drum arranged with indicia, as well as a connection mechanism arranged between said dose setting nut and said dose drum such that said dose drum is rotated together with the dose setting nut when operated for setting a dose, displaying the set dose.

4. The medicament delivery device according to claim 3, wherein said connection mechanism is arranged as a releasable connection.

5. The medicament delivery device according claim 4, wherein said connection mechanism comprises resiliently arranged protrusions on one of said dose nut or dose drum engageable with cut-outs on the other of said dose drum or dose nut.

6. The medicament delivery device according to claim 4, further comprising a return force element operably connected to said dose drum such that the return force element is tensioned when a dose is set.

7. The medicament delivery device according to claim 6, further comprising a release mechanism operably connected to said activator, wherein, when said activator is activated, said release mechanism is arranged to act on said connection mechanism for releasing said dose drum from said dose setting nut, whereby said return force element is capable of moving said dose drum back to its initial position.

8. The medicament delivery device according to claim 1, further comprising a dose limiting mechanism operably arranged to said dose nut and capable of limiting the maximum dose to be set.

9. The medicament delivery device according to claim 8, wherein said dose limiting mechanism comprises a stop ledge arranged to interact with a stop ledge on said housing, wherein the turning of the dose nut will bring the stop ledges in contact with each other within one turn of the dose setting nut, limiting the maximum dose to be set.

10. The medicament delivery device according to claim 1, further comprising a dose positioning mechanism operably arranged between said medicament container holder and said housing, capable of providing distinct fixed positions in the longitudinal direction of the medicament container holder in relation to the housing when a dose is set.

11. The medicament delivery device according to claim 10, wherein said dose positioning mechanism comprises positioning elements arranged on said housing, capable of engaging said second threads of said medicament container holder.

12. The medicament delivery device according to claim 11, wherein said activator comprises a locking mechanism operably connected to said dose positioning mechanism such that, when said activator is operated, said positioning elements are in locked engagement with said second threads of said medicament container holder.

13. The medicament delivery device according to claim 1, further comprising a last dose mechanism operably arranged to said dose nut and capable of limiting the maximum dose to be set to the remaining quantity of medicament in said medicament container.

14. The medicament delivery device according to claim 13, wherein said last dose mechanism comprises a stop ledge in a proximal area of said medicament container holder, arranged to come in contact with, and limit the movement, of said dose setting nut.

15. The medicament delivery device according to claim 1, wherein said activator comprises a manually operable push button extending in a distal direction through the housing.

16. The medicament delivery device according to claim 10, wherein said activator comprises a return force element arranged to return said activator after delivery of a dose of medicament.

17. A medicament delivery device comprising:
a housing;
a medicament container holder arranged movable in relation to the housing and capable of accommodating a medicament container;
a dose setting drum arranged with indicia;
a dose setting nut having first threads;
a connection mechanism arranged between the dose setting nut and the dose drum such that the dose drum is rotated together with the dose setting nut when operated for setting a dose, displaying the set dose; and
an activator arranged in the housing and capable of, upon activation, acting on a medicament container for expelling a dose of medicament, where the activator comprises:
a plunger rod that moves proximally relative to the medicament container during delivery of the set dose and automatically moves distally relative to the medicament container after the set dose is delivered;
and
second threads arranged on the medicament container holder being arranged to cooperate with the first threads on the dose setting nut,
wherein operation of the dose setting nut will cause the medicament container holder with the medicament container to move towards the plunger rod for setting a dose of medicament to be delivered.

18. The medicament delivery device according claim 17, wherein the connection mechanism is releasable and comprises resiliently arranged protrusions on one of the dose nut or dose drum engageable with cut-outs on the other of the dose drum or dose nut.

19. The medicament delivery device according to claim 17, further comprising a last dose mechanism operably arranged to the dose nut and capable of limiting the maximum dose to be set to the remaining quantity of medicament in the medicament container.

20. The medicament delivery device according to claim 19, wherein the dose limiting mechanism comprises a stop ledge arranged to interact with a stop ledge on the housing, wherein the turning of the dose nut will bring the stop ledges in contact with each other within one turn of the dose setting nut, limiting the maximum dose to be set.

* * * * *